United States Patent
Nakajima

(10) Patent No.: US 10,031,147 B2
(45) Date of Patent: Jul. 24, 2018

(54) AUTOMATIC ANALYZER AND MAINTENANCE SUPPORTING SYSTEM

(71) Applicant: Hitachi High-Technologies Corporation, Tokyo (JP)

(72) Inventor: Atsushi Nakajima, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 35 days.

(21) Appl. No.: 14/416,376

(22) PCT Filed: Jul. 23, 2013

(86) PCT No.: PCT/JP2013/069936
§ 371 (c)(1),
(2) Date: Jan. 22, 2015

(87) PCT Pub. No.: WO2014/017494
PCT Pub. Date: Jan. 30, 2014

(65) Prior Publication Data
US 2015/0260742 A1     Sep. 17, 2015

(30) Foreign Application Priority Data
Jul. 23, 2012 (JP) .................. 2012-162307

(51) Int. Cl.
*G01N 35/00* (2006.01)
*G01N 35/04* (2006.01)
*G05B 19/4062* (2006.01)

(52) U.S. Cl.
CPC . *G01N 35/00613* (2013.01); *G01N 35/00623* (2013.01); *G01N 35/04* (2013.01);
(Continued)

(58) Field of Classification Search
CPC .......... G01N 2035/00643; G01N 2035/00653; G01N 35/00623
See application file for complete search history.

(56) References Cited

U.S. PATENT DOCUMENTS

2001/0051841 A1* 12/2001 Kawai .................. B23Q 11/04
700/175
2005/0281707 A1* 12/2005 Nakaya ............ G01N 35/00594
422/63
(Continued)

FOREIGN PATENT DOCUMENTS

JP        07129236         5/1995
JP       2000116980        4/2000
(Continued)

OTHER PUBLICATIONS

International Search Report in PCT/JP2013/069936, dated Oct. 15, 2013.
Written Opinion in PCT/JP2013/069936, dated Oct. 15, 2013.

*Primary Examiner* — P. Kathryn Wright
(74) *Attorney, Agent, or Firm* — Mattingly & Malur, PC

(57) ABSTRACT

Provided are an automatic analysis device and a maintenance support system which prevent a failure that occurs between regular inspection periods to thereby reduce the downtime of the automatic analysis device. A maintenance support system acquires, from each of a plurality of automatic analysis devices (100), pulse information transmitted from the automatic analysis device (100) provided with a mechanism which is driven by a pulse motor, and a transmission means which transmits pulse information including tow among a driving pulse value for driving the pulse motor, a consumed pulse amount that is a pulse amount consumed when the pulse motor has actually been driven, and a remaining pulse amount obtained by subtracting the consumed pulse amount from the driving pulse value, and stores at least the consumed pulse amount.

12 Claims, 10 Drawing Sheets

(52) U.S. Cl.
CPC ............ *G05B 19/4062* (2013.01); *G01N 2035/00643* (2013.01); *G01N 2035/00653* (2013.01); *G01N 2035/0439* (2013.01); *G01N 2035/0446* (2013.01); *G01N 2035/0496* (2013.01); *G05B 2219/32234* (2013.01); *G05B 2219/37209* (2013.01); *G05B 2219/45092* (2013.01)

(56) References Cited

U.S. PATENT DOCUMENTS

| | | | |
|---|---|---|---|
| 2009/0215183 A1* | 8/2009 | Takehara | G01N 35/00623 436/47 |
| 2011/0184536 A1* | 7/2011 | Tanoshima | G01N 35/00871 700/73 |
| 2012/0283980 A1* | 11/2012 | Suga | G01N 35/00871 702/108 |

FOREIGN PATENT DOCUMENTS

| | | |
|---|---|---|
| JP | 2001004635 | 1/2001 |
| JP | 2008089615 | 4/2008 |
| JP | 2009204386 | 9/2009 |

* cited by examiner

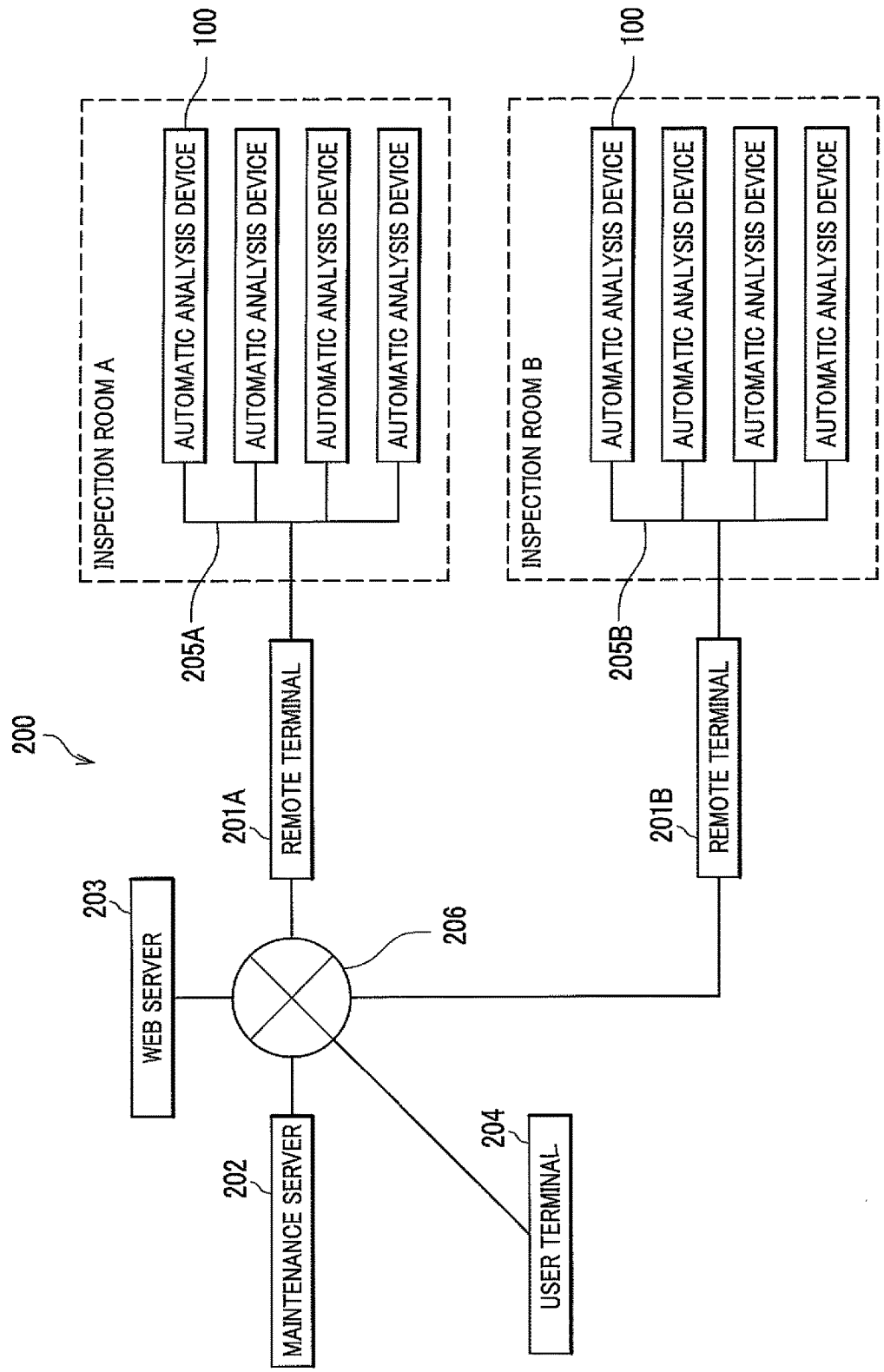

FIG.3B

| | | | |
|---|---|---|---|
| | MECHANISM B | MOTOR No1 | NUMBER OF DRIVING TIMES 1 | DRIVING PULSE VALUE |
| | | | | CONSUMED PULSE QUANTITY |
| | | | | REMAINING PULSE QUANTITY |
| | | | NUMBER OF DRIVING TIMES 2 | DRIVING PULSE VALUE |
| | | | | CONSUMED PULSE QUANTITY |
| | | | | REMAINING PULSE QUANTITY |
| | ... | | |
| | ... | | |
| AUTOMATIC ANALYSIS DEVICE 2 | MECHANISM A | MOTOR No1 | ... |
| | ... | | |
| | MECHANISM n | MOTOR No1 | ... |
| | ... | | |
| INSPECTION ROOM 2 | | | |
| AUTOMATIC ANALYSIS DEVICE 1 | MECHANISM A | MOTOR No1 | ... |
| INSPECTION ROOM 3 | | | |
| AUTOMATIC ANALYSIS DEVICE 1 | MECHANISM A | MOTOR No1 | ... |
| ... | | | |

FIG.4

PULSE MOTOR AVERAGE VALUE TABLE

| AUTOMATIC ANALYSIS DEVICE MODEL A | | |
|---|---|---|
| MECHANISM A | MOTOR 1 (DRIVING PULSE VALUE 90) | AVERAGE NUMBER OF AT-FAILURE DRIVING TIMES |
| | | AVERAGE AT-FAILURE PULSE QUANTITY |
| | | DEVIATION RATE FROM AVERAGE PULSE QUANTITY (%) |
| | | APPROXIMATION RATE TO AT-FAILURE PULSE QUANTITY (%) |
| | MOTOR 1 (DRIVING PULSE VALUE 50) | AVERAGE NUMBER OF AT-FAILURE DRIVING TIMES |
| | | AVERAGE AT-FAILURE PULSE QUANTITY |
| | | DEVIATION RATE FROM AVERAGE PULSE QUANTITY (%) |
| | | APPROXIMATION RATE TO AT-FAILURE PULSE QUANTITY (%) |
| | ... | |
| | MOTOR n (DRIVING PULSE VALUE n) | AVERAGE NUMBER OF AT-FAILURE DRIVING TIMES |
| | | AVERAGE AT-FAILURE PULSE QUANTITY |
| | | DEVIATION RATE FROM AVERAGE PULSE QUANTITY (%) |
| | | APPROXIMATION RATE TO AT-FAILURE PULSE QUANTITY (%) |
| MECHANISM B | MOTOR 1 | AVERAGE NUMBER OF AT-FAILURE DRIVING TIMES |
| | | AVERAGE AT-FAILURE PULSE QUANTITY |
| | | DEVIATION RATE FROM AVERAGE PULSE QUANTITY (%) |
| | | APPROXIMATION RATE TO AT-FAILURE PULSE QUANTITY (%) |
| | ... | |
| | MOTOR n | ... |
| ... | | |
| MECHANISM n | MOTOR 1 | ... |
| AUTOMATIC ANALYSIS DEVICE MODEL B | | |
| MECHANISM A | ... | ... |

FIG.6

| MOTOR No | STATE OF PULSE MOTOR (OF INDIVIDUAL AUTOMATIC ANALYSIS DEVICE) ||||
|---|---|---|---|---|
| | INSPECTION ROOM 1 ||||
| | AUTOMATIC ANALYSIS DEVICE 1 ▼ ||||
| | MECHANISM A | MECHANISM B | MECHANISM C | MECHANISM N |
| 1 | ○ | ○ | △ | ○ |
| 2 | ○ | ○ | ○ | ○ |
| 3 | ○ | ○ | ○ | ○ |
| 4 | ○ | ○ | — | ○ |
| 5 | ○ | △ | — | ○ |
| 6 | ○ | × | — | ○ |
| 7 | ○ | — | — | ○ |
| ... | ... | ... | ... | ... |
| n | ○ | — | — | ○ |

BACK  NEXT  CLOSE

FIG.7

STATE OF PULSE MOTORS (OF INDIVIDUAL INSPECTION ROOM)

| DEVICE LIST | | | | | |
|---|---|---|---|---|---|
| INSPECTION ROOM 1 | AUTOMATIC ANALYSIS DEVICE 1 | AUTOMATIC ANALYSIS DEVICE 2 | AUTOMATIC ANALYSIS DEVICE 3 | ... | AUTOMATIC ANALYSIS DEVICE N |
| INSPECTION ROOM 2 | AUTOMATIC ANALYSIS DEVICE 1 | AUTOMATIC ANALYSIS DEVICE 2 | AUTOMATIC ANALYSIS DEVICE 3 | | — |
| INSPECTION ROOM 3 | AUTOMATIC ANALYSIS DEVICE 1 | AUTOMATIC ANALYSIS DEVICE 2 | | | — |
| INSPECTION ROOM 4 | AUTOMATIC ANALYSIS DEVICE 1 | | | | — |
| INSPECTION ROOM 5 | AUTOMATIC ANALYSIS DEVICE 1 | AUTOMATIC ANALYSIS DEVICE 2 | — | | — |
| ... | | | | | ... |
| INSPECTION ROOM N | AUTOMATIC ANALYSIS DEVICE 1 | AUTOMATIC ANALYSIS DEVICE 2 | | | — |

CLOSE

FIG.8

| MOTOR No | MECHANISM A | MECHANISM B | MECHANISM C | | MECHANISM N |
|---|---|---|---|---|---|
| \multicolumn{6}{l}{INPUT DEVIATION RATE FROM AVERAGE CONSUMED PULSE QUANTITY} | | | | | |

| INPUT DEVIATION RATE FROM AVERAGE CONSUMED PULSE QUANTITY ▼ |
|---|
| AUTOMATIC ANALYSIS DEVICE MODEL A ▼ |

| MOTOR No | MECHANISM A | MECHANISM B | MECHANISM C | MECHANISM N |
|---|---|---|---|---|
| 1 | 10% | 10% | 10% | 10% |
| 2 | 5% | 10% | 10% | 10% |
| 3 | 5% | 10% | 10% | 10% |
| 4 | 3% | 10% | 10% | 10% |
| 5 | 10% | — | — | 10% |
| 6 | 10% | — | — | 5% |
| 7 | 10% | — | — | 5% |
| ... | | | | ... |
| n | 5% | — | | 10% |

[ BACK ] [ NEXT ] [ CLOSE ]

AUTOMATIC ANALYZER AND MAINTENANCE SUPPORTING SYSTEM

TECHNICAL FIELD

The present invention relates to an automatic analyzer and a maintenance supporting system.

BACKGROUND ART

For example, there is known an automatic analysis device for qualitative/quantitative analysis of a biological sample, such as blood and urine.

Service companies periodically perform maintenance of respective mechanisms of an automatic analysis device in order to operate the automatic analysis device in normal conditions. Maintenance includes a case of performing component replacement due to duration of use, based on starting inspection, finishing inspection, periodic inspection, or the like, and a case of notifying an alarm to a service company when an automatic analysis device has fallen into an abnormal state and performing component replacement through checking and maintenance, as necessary, of the conditions of respective mechanisms.

SUMMARY OF THE INVENTION

Problems to be Solved by the Invention

For normal operation of an automatic analysis device, expiration dates are placed on the respective components of the automatic analysis device, and a service person of a service company performs periodic replacement of mechanism components. Thus, failure of components due to aging is prevented, and down time of the automatic analysis device is reduced.

However, even during an interval between periodic inspections, in some cases, abnormality occurs due to high usage frequency of a component or an unexpected external factor, and component replacement is performed. Incidentally, for a conventional automatic analysis device, component replacement is performed, according to an alarm output from an automatic analysis device or a certain period of time as an indication for replacing a mechanism component.

In this situation, an object of the present invention is to provide automatic analysis devices and a maintenance support system for preventing failures occurring during a cycle, of periodic inspections and reducing down time of the automatic analysis devices.

Means for Solving the Problem

In order to solve the above-described problem, an automatic analysis device according to the present invention includes: a mechanism driven by a pulse motor; and transmitting means for transmitting pulse information including two out of a driving pulse value for driving the pulse motor, a consumed pulse quantity that is a quantity of pulses having been consumed during actual driving of the pulse motor, and a remaining pulse quantity that is obtained by subtracting the consumed pulse quantity from the driving pulse value.

Further, a maintenance support system according to the invention obtains pulse information transmitted from plural automatic analysis devices; accumulates at least consumed pulse quantities; determines whether or not an obtained consumed pulse quantity of a pulse motor deviates, by a predetermined deviation rate or more, from an average consumed pulse quantity that is an average value of the accumulated consumed pulse quantities; and determines that the pulse motor is in an abnormal tendency if the deviation has been determined.

Still further, the maintenance support system determines whether or not the obtained consumed pulse quantity of the pulse motor approximates to an average at-failure pulse quantity that is an average value of consumed pulse quantities at failure occurrence on pulse motors, by a predetermined approximation rate or more; and determines that the pulse motor is in an abnormal tendency of if the approximation has been determined.

Advantage of the Invention

According to the present invention, it is possible to provide automatic analysis devices and a maintenance support system for preventing failures occurring during a cycle of periodic inspections and reducing down time of the automatic analysis devices.

BRIEF DESCRIPTION OF THE DRAWINGS

FIG. 2 is a structural block diagram of a maintenance support system for the automatic analysis device in the present embodiment;

FIG. 3A and FIG. 3B show an example of a table of pulse information accumulated in a maintenance server;

FIG. 4 shows an example of a pulse motor average value table stored in the maintenance server;

FIG. 6 shows an example of a screen displaying states of pulse motors in an individual automatic analysis device;

FIG. 7 shows an example of a screen displaying states of automatic analysis devices;

FIG. 8 shows an example of an input screen for input of a deviation rate and an approximation rate.

EMBODIMENT FOR CARRYING OUT THE INVENTION

Figure 1:
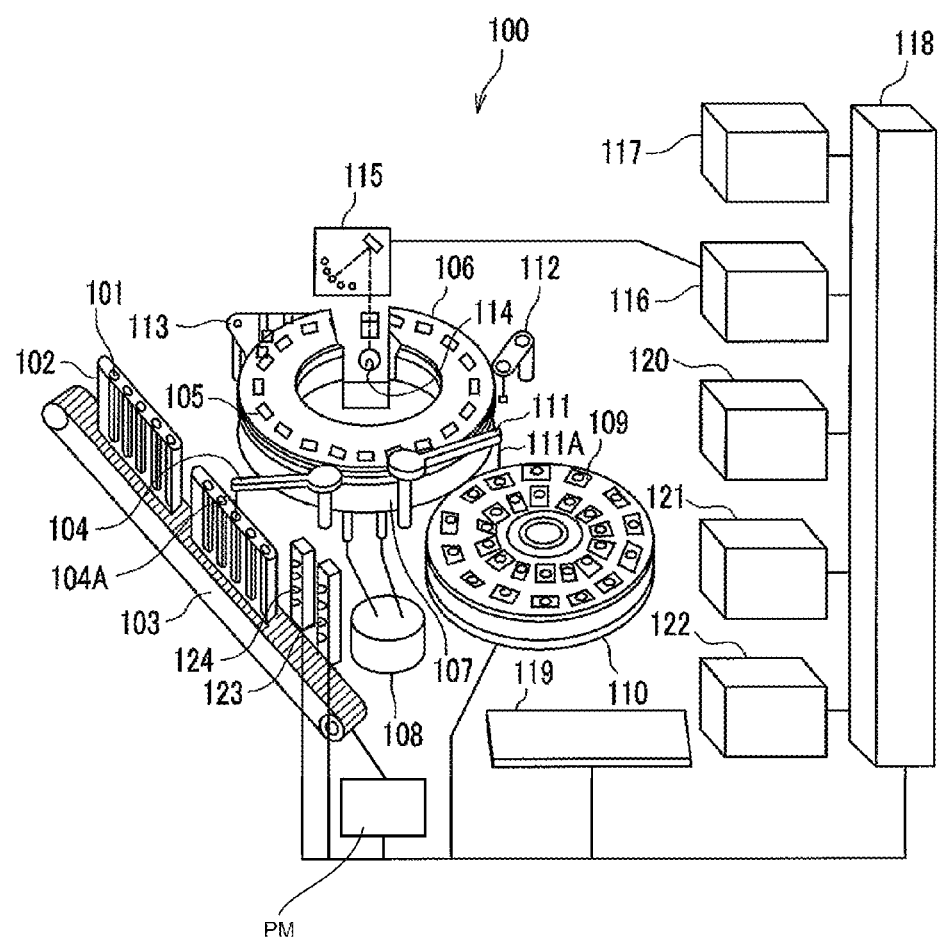
FIG. 1 is a schematic structural diagram of an automatic analysis device in the present embodiment.

An embodiment for carrying out the present invention (hereinafter, referred to as 'embodiment') will be described below in detail, referring to the drawings, as appropriate. Incidentally, the same symbol will be assigned to a common element in the respective drawings, and overlapping description will be omitted.

(Automatic Analysis Device)

The structure of an automatic analysis device 100 in the present embodiment will be described, using FIG. 1. FIG. 1 is a schematic structural diagram of the automatic analysis device 100 in the present embodiment. Incidentally, in the following description, the automatic analysis device 100 will be described as one for measuring absorbance of light, however, the invention is not limited thereto.

The automatic analysis device 100 includes a rack transportation device 103 for transporting specimen racks 102 on which plural specimen containers 101 containing specimen are mounted, a specimen dispensing mechanism 104, a reaction disc 106 on which plural reaction containers 105 are mounted on a concentric circle, a heat retaining bath 107, a constant temperature bath 108, a reagent disc 110 on which plural reagent bottles 109 containing various reagents are mounted on a concentric circle, a reagent dispensing mechanism 111, an agitation device 112, a cleaning device 113, a light source 114, a multi-wavelength photometer 115, an A/D convertor 116, a computer 117, an interface 118, an input device 119, a printer 120, a monitor 121, a storage device 122, a rack number reading device 123, and a specimen ID reading device 124.

The rack transportation device 103 is configured to be able to transport, along a transportation line, the specimen racks 102, on which plural specimen containers 101 containing specimen are mounted on the rotation circumference of the specimen dispensing mechanism 104 and along a tangent line of the reaction disc 106. Incidentally, the rack transportation device 103 is driven by a pulse motor PM and controlled by the computer 117 via the interface 118. For simplicity, the individual pulse motors which drive the specimen dispensing mechanism 104, the reaction disk 106 and the like as described below are omitted in FIG. 1.

The rack number reading device 123 and the specimen ID reading device 124 are disposed along the transportation line of the rack transportation device 103. Incidentally, information having been read by the rack number reading device 123 and the specimen ID reading device 124 is input via the interface 118 to the computer 117.

The specimen dispensing mechanism 104 is configured to be able to dispense a predetermined amount of the specimen in a specimen container 101 into a reaction container 105, using a specimen dispensing probe 104A and under control by the computer 117. The specimen dispensing mechanism 104 has a rotation driving mechanism (not shown) for moving the specimen dispensing probe 104A between the specimen container 101 and the reaction container 105. Further, the specimen dispensing mechanism 104 has a driving mechanism (not shown) for vertically moving the specimen dispensing probe 104A. Incidentally, the rotation driving mechanism and the driving mechanism of the specimen dispensing mechanism 104 are configured to be driven by a pulse motor and controlled via the interface 118 by the computer 117.

On the reaction disc 106, plural reaction containers 105 are disposed on a circle concentric with the reaction disc 106. The reaction disc 106 is rotatably installed and has a rotation driving mechanism (not shown). The rotation driving mechanism of the reaction disc 106 is driven by a pulse motor and is controlled via the interface 118 by the computer 117. Incidentally, the reaction disc 106 is configured to be maintained at a predetermined temperature by the heat retaining bath 107 communicated with the constant temperature bath 108.

On the reagent disc 110, plural reagent bottles 109 containing various reagent are mounted on a circle concentric with the reagent disc 110. The reagent disc 110 is rotatably installed and has a rotation driving mechanism (not shown). The rotation driving mechanism of the reagent disc 110 is driven by a pulse motor and is controlled via the interface 118 by the computer 117.

The reagent dispensing mechanism 111 is configured to be able to dispense a predetermined amount of the reagent in a reagent bottle 109 into a reaction container 105, using a reagent dispensing probe 111A and under control by the computer 117. The reagent dispensing mechanism 111 has a rotation driving mechanism (not shown) for moving the reagent dispensing probe 111A between the reagent bottle 109 and the reaction container 105. Further, reagent dispensing mechanism 111 has a driving mechanism (not shown) for vertically moving the reagent dispensing probe 111A. Incidentally, the rotation driving mechanism and the driving mechanism of the reagent dispensing mechanism 111 are configured to be driven by a pulse motor and controlled via the interface 118 by the computer 117.

The agitation device 112 is configured to be able to agitate specimen and reagent dispensed in a reaction container 105. Incidentally, the agitation device 112 has a driving mechanism (not shown). Incidentally, the driving mechanism of the agitation device 112 is driven by a pulse motor and controlled via the interface 118 by the computer 117.

The cleaning device 113 is configured to be able to clean the reaction containers 105. Incidentally, the agitation device 112 has a driving mechanism (not shown). Incidentally, the driving mechanism of the cleaning device 113 is configured to be driven by a pulse motor and controlled via the interface 118 by the computer 117.

The multi-wavelength photometer 115 is configured to be able to measure the absorbance of light of the liquid (reaction solution) in a reaction container 105, using the light source 114. A measured absorbance signal is converted by the A/D convertor 116 from an analog signal into a digital signal to be input via the interface 118 to the computer 117.

The computer 117 is configured to be able to control the entire automatic analysis device 100 by controlling the respective mechanisms. The computer 117 is connected via the interface 118 with the input device 119 for input of various operation conditions, the printer 120 and the monitor 121, which are output devices, and the storage device 122 for storing various data.

The computer 117 controls the rack transportation device 103 to transport the specimen racks 102. An individual serial number (rack number) is assigned to the each specimen rack 102, and the each serial number is read by the rack number reading device 123 during when the specimen rack 102 is transported on the transportation line. Further, when a specimen ID number is assigned to the specimen container 101 held by a specimen rack 102, the specimen ID number is read by the specimen ID reading device 124. Incidentally, information having been read by the rack number reading device 123 and the specimen ID reading device 124 is input via the interface 118 to the computer 117.

The computer 117 controls the rack transportation device 103 to move the specimen racks 102 until a first specimen container 101 held by a specimen rack 102 comes to a position directly under the specimen dispensing probe 104A of the specimen dispensing mechanism 104. Then, the computer 117 controls the specimen dispensing mechanism 104 to dispense a predetermined amount of the reagent contained in the first specimen container 101 into a first reaction container 105, using the specimen dispensing probe 104A.

Similarly, the computer 117 controls the rack transportation device 103 and moves the specimen racks 102 until a second specimen container 101 held by a specimen rack 102 comes to the position directly under the specimen dispensing probe 104A of the specimen dispensing mechanism 104. Further, the computer 117 controls the reaction disc 106 to rotate it by a predetermined angle. Then, the computer 117 controls the specimen dispensing mechanism 104 to dispense a predetermined amount of the reagent contained in the second specimen container 101 into a second reaction container 105, using the specimen dispensing probe 104A. Subsequently, the rest of specimens are dispensed similarly into reaction containers 105.

A reaction container 105 into which a specimen has been dispensed rotates and moves on the reaction disc 106 by a rotation operation of the reaction disc 106. Meanwhile, the computer 117 controls the reagent disc 110 to move it until a reagent bottle 109 containing a certain reagent comes to a position directly under the reagent dispensing probe 111A of the reagent dispensing mechanism 111. Then, the computer 117 controls the reagent dispensing mechanism 111 to dispense the reagent contained in the reagent bottle 109 into the reaction container 105 by a predetermined amount, using the reagent dispensing probe 111A. Then, the computer 117 controls the agitation device 112 to agitate liquid (reaction solution) of the specimen and the reagent having been dispensed into the reaction container 105.

Then, the absorbance of light of the liquid (reaction solution) in the reaction container 105 is measured with the light source 114 and the multi-wavelength photometer 115, and a signal of the measured absorbance is converted by the A/D convertor 116 into a digital signal to be input via the interface 118 to the computer 117. A reaction container 105 on which analysis has been finished is cleaned by the cleaning device 113.

The computer 117 converts the absorbance into the concentration of the component of the measuring object in the specimen, and creates data that is associated with information (rack number, specimen ID) having been read by the rack number reading device 123 and the specimen ID reading device 124. The created data is printed out from the printer 120 via the interface 118, displayed in a screen on the monitor 121, and stored in the storage device 122.

(Control of Pulse Motor and Detection of Abnormal Tendency)

Herein, as described above, in the automatic analysis device 100 in the present embodiment, mechanisms are arranged such that the rack transportation device 103, the specimen dispensing mechanism 104, the reaction disc 106, the reagent disc 110, the reagent dispensing mechanism 111, the agitation device 112, and the cleaning device 113 are driven by pulse motors.

The operation speeds (operation angular velocities) and the operation distances (operation angles) of the respective mechanisms are controlled by pulses (electrical power transmission amount) to the pulse motors. Taking into account faults by aging, noises, and the like of the respective components of a mechanism, a pulse value, which is larger than the pulse value for an operation speed (operation angular velocity) and an operation distance (operation angular velocity) as the operation purpose, is set as a driving pulse value. On the other hand, there are also mechanisms that perform control, using sensors (not shown) such that operation distances (operation angles) do not exceed the operation distances (operation angles) as the operation purpose of mechanism.

The computer 117 of the automatic analysis device 100 in the present embodiment is configured to store and accumulate driving pulse values and consumed pulse quantities in the storage device 122, recognizing a pulse quantity having been consumed, on a driving pulse value for driving a pulse motor, during actual driving of the pulse motor as a consumed pulse quantity. Further, remaining pulse quantities, each of which is obtained by subtracting a consumed pulse quantity from a driving pulse value, are also stored and accumulated in the storage device 122.

Herein, if some failure has occurred or aging has proceeded on a mechanism driven by a pulse motor, the consumed pulse quantity becomes a value that gradually deviates from a driving pulse value, and later deviates up to a value that prohibits operation for the purpose, and phenomenon of some failure occurs.

In this situation, the computer 117 of an automatic analysis device 100 in the present embodiment functions as means for transmitting information of the driving pulse values, the consumed pulse quantities, and the remaining pulse quantities of a pulse motor stored and accumulated in the storage device 122, to a maintenance support system 200 (a later described maintenance server 202 (see FIG. 2)) in the present embodiment via the interface 118. Further, in addition to the information of the driving pulse values, the consumed pulse quantities, and the remaining pulse quantities, it is also possible to transmit the number of driving times and the failure state of the pulse motor.

The maintenance support system 200 (see the later-described FIG. 2) in the present embodiment is configured to be able to specify a mechanism with a pulse motor in a tendency of abnormality, in other words, a mechanism with a possibility of occurrence of failure, by collecting, accumulating, and monitoring driving pulse values, consumed pulse quantities, and remaining pulse quantities from plural facilities where automatic analysis devices 100 are installed. Further, by adding the specified mechanism to the check items of periodical inspection, it is possible to prevent failures occurring during a cycle of periodic inspections and reducing down time of the automatic analysis device 100.

Further, by performing statistical processing of such information collected from the respective facilities, it is also possible to update in real time the number of driving time, of a mechanism, up to causing a failure, predict an appropriate time of component replacement, and specify a mechanism that needs improvement. Still further, it is possible to detect a mechanism with a high failure frequency in an automatic analysis device 100, and thereby obtain a target of improvement in an automatic analysis device in operation or an automatic analysis device under development.

(Maintenance Support System for Automatic Analysis Devices)

In the following, the maintenance support system 200 for automatic analysis devices 100 will be described, referring to FIG. 2. FIG. 2 is a structural block diagram of the maintenance support system 200 for the automatic analysis devices 100 in the present embodiment. Incidentally, in the example in FIG. 2, it is assumed that there are two inspection rooms (inspection room A and inspection room B), and plural (four in the example in FIG. 2) automatic analysis devices 100 are installed in the each inspection room.

As shown in FIG. 2, the maintenance support system 200 for automatic analysis devices 100 is provided with remote terminals 201A, 201B, a maintenance server 202, and a WEB server 203, which are connected by communication lines 205A, 205B, and 206. Incidentally, symbol 204 represents a user terminal.

The remote terminal 201A is connected with automatic analysis devices 100 installed in the inspection room A via the communication line (for example, LAN (Local Area Network)) 205A. The remote terminal 201B is connected with automatic analysis devices 100 installed in the inspection room B via the communication line (for example, LAN) 205B.

The remote terminals 201A, 201B are communicatably connected with the maintenance server 202 via the communication line (for example, a dedicated line or Internet connection) 206. Further, the maintenance server 202, the WEB server 203, and the user terminal 204 are communicatably connected via the communication line 206.

The each automatic analysis device 100 is configured to be able to transmit the driving pulse value, the consumed pulse quantity, and the remaining pulse quantity of a pulse motor arranged for a corresponding mechanism, via the remote terminal 201A or 201B to the maintenance server 202. Incidentally, in the following description, driving pulse values, consumed pulse quantities, and remaining pulse quantities, which are output from the respective automatic analysis devices 100, will be collectively referred to as pulse information.

Herein, the relationship between a driving pulse value, a consumed pulse quantity, and a remaining pulse quantity satisfies the following Expression (1).

$$\text{Remaining pulse quantity} = \text{Driving pulse value} - \text{Consumed pulse quantity} \quad (1)$$

An automatic analysis device 100 is configured to be able to transmit a notification of occurrence of failure together with pulse information to the maintenance server 202 in case that a failure has occurred on a pulse motor arranged for the corresponding mechanism.

The maintenance server 202 is configured to be able to obtain and accumulate pulse information on pulse motors arranged for the respective mechanisms of an automatic analysis device 100 via the remote terminal 201A or 201B. Incidentally, a pulse information table 300 in which pulse information is accumulated will be described later, referring to FIG. 3.

Further, in case that the maintenance server 202 has received a notification of failure occurrence on a pulse motor arranged for the corresponding mechanism of an automatic analysis device 100, the maintenance server 202 can compute the average values of various information of pulse motors at the times of failure occurrence and store the computed average values. Incidentally, a pulse motor average value table 400 at failure occurrence will be described later, referring to FIG. 4.

Further, the maintenance server 202 is configured to be able to determine whether or not a pulse motor, whose pulse information has been obtained, has a possibility of occurrence of failure, based on the pulse information table 300 (see FIG. 3) and the pulse motor average value table 400 (see FIG. 4). If the maintenance server 202 has determined a possibility of occurrence of failure, the maintenance server 202 can notify the user terminal 204 of this determination by a mail.

Herein, determination on whether or not there is a possibility of occurrence of failure is made, for example, such that a possibility of occurrence of failure is determined if the consumed pulse quantity of a pulse motor has deviated by a predetermined or a larger quantity from the average value of consumed pulse quantities of pulse motors in all the inspection rooms, or has approximated to a failure value (the average value at the times of failure occurrence). Incidentally, determination on whether or not a failure possibly occurs will be described later, referring to FIG. 5.

The WEB server 203 is configured to be able to obtain pulse information and the like from the maintenance server 202, and store a screen 500 (see FIG. 5 described later) displaying graphs, a screen 600 (see FIG. 6 described later) displaying the states of the respective mechanisms of a single automatic analysis device 100, and a screen 700 (see FIG. 7 described later) displaying the states of automatic analysis devices 100.

The user terminal 204 is a terminal installed in a service company for services of maintenance and inspection and the like of automatic analysis devices 100, and is connected to the WEB server 203 via the communication line 206 to be able to refer to screens (FIG. 5, FIG. 6, and FIG. 7 described later) stored in the WEB server 203.

The user terminal 204 is configured to be able to display an input screen 800 (see FIG. 8 described later) and input a deviation rate and an approximation rate for determination of possibility of failure occurrence.

(Pulse Information Table)

In the following, an example of a pulse information table 300, in the maintenance server 202, for accumulating pulse information will be described, referring to FIG. 3.

Figure 3A:
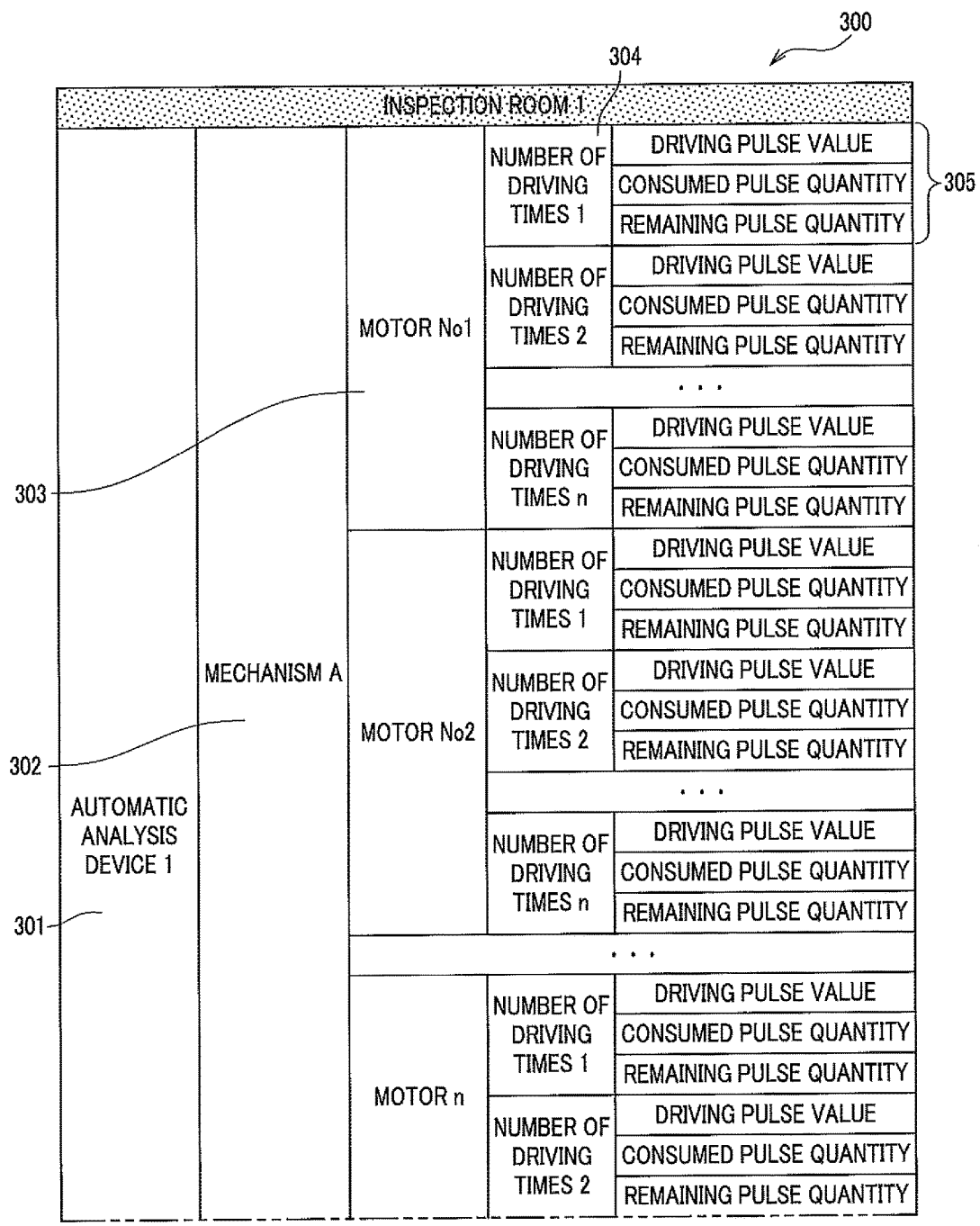

The pulse information table 300 for storing pulse information of pulse motors is, as shown in FIG. 3, formed with the automatic analysis device numbers 301 of automatic analysis devices 100 installed in respective inspection rooms, the mechanism numbers 302 of respective mechanisms configuring the automatic analysis devices 100, the pulse motor numbers 303 of pulse motors configuring the mechanisms, and pulse information 305 for the respective numbers of driving times 304 of the pulse motors. The pulse information 305 is formed with driving pulse values, consumed pulse quantities, and remaining pulse quantities.

In such a manner, pulse information of all the mechanisms of the automatic analysis devices 100 installed in all the inspection rooms is accumulated in the maintenance server 202.

(Pulse Motor Average Value Table)

In the following, an example of the pulse motor average value table 400, in the maintenance server 202, for storing average values at failure occurrence will be described, referring to FIG. 4.

The pulse motor average value table 400 stores various average values computed from the numbers of driving times at failure occurrence on pulse motors and pulse information (driving pulse value, consumed pulse quantity, and remaining pulse quantity), which have been extracted out from the pulse information, of all the inspection rooms, accumulated in the pulse information table 300 (see FIG. 3).

As shown in FIG. 4, the pulse motor average value table 400 is formed for an individual model 401 of automatic analysis device 100. Further, the pulse motor average value table 400 stores the average numbers of at-failure driving times 405, which are obtained by computing the averages of numbers of driving times at the time of failure occurrence, and the average at-failure pulse quantities 406, which are obtained by computing the averages of consumed pulse quantities at the time of failure occurrence, for the respective mechanism numbers 402, the respective pulse motor numbers 403, and the respective driving pulse values 404.

Further, the deviation rates (deviation rates from the average pulse quantities) 407 of deviations from the average consumed pulse quantities (see graph 506 in FIG. 5 described later) for detecting the possibility of failure occurrence on a pulse motor are stored. Still further, the approximation rates (approximation rates to at-failure pulse quantities) 408 to the average at-failure pulse quantities 406 (see graph 507 in FIG. 5 described later) for detecting the possibility of failure occurrence on a pulse motor are stored. Incidentally, deviation rates 407 and approximation rates 408 may be a preset value and may be, as described later, a value input via an input screen 800 (see FIG. 8).

(Screen for Displaying Variation in Consumed Pulse Quantity of Individual Pulse Motor)

In the following, an example of a screen 500, which is stored in the WEB server 203 and displayed on the user terminal 204, for displaying graphs representing variation in the consumed pulse quantity of an individual motor will be described, referring to FIG. 5.

The graphs on the screen 500 represent a pulse quantity 501 by y-axis (vertical axis) and a number of driving times 502 by x-axis (horizontal axis). The graphs are created for an individual driving pulse value 504 of a pulse motor 503 as an object.

The graph 505 is a graph of consumed pulse quantities plotted for a corresponding individual driving pulse value 504 of a pulse motor 503 to be an object.

The graph 506 is a graph of average consumed pulse quantities of the same pulse motors (pulse motors installed at the same position of the same mechanism of the same model) as the pulse motor 503 to be an object in terms of motor, having all the facilities as the object of averaging.

The graph 507 is a graph of averages of the consumed pulse quantities at failure occurrence on the same pulse motors (the average at-failure pulse quantities 406 in FIG. 4).

Herein, determination of a possibility of failure occurrence on a pulse motor by the maintenance server 202 will be described, referring to FIG. 5.

A possibility of failure occurrence is determined if the graph 505 has deviated from the graph 506 of plotted average consumed pulse quantities by a predetermined deviation rate (the average pulse quantity deviation rate 407 in FIG. 4) or more. Further, a possibility of failure occurrence is also determined if the graph 505 has approximated to the graph 507 representing the average at-failure pulse quantities 406 by a predetermined approximation rate (approximation rate to at-failure pulse quantity 408 in FIG. 4) or more. Incidentally, if a possibility of failure occurrence has been determined, for example, the display color of the graph 505 is changed for visual recognition of the possibility of a failure.

(Screen for Displaying Pulse Motor States of Individual Automatic Analysis Device)

In the following, an example of a screen 600, displayed on the user terminal 204, for displaying the states of the pulse motors of an individual automatic analysis device will be described, referring to FIG. 6.

The screen 600 shown in FIG. 6 is displayed for an individual automatic analysis device 601 and displayed in a matrix structure 602, wherein respective mechanisms of an automatic analysis device are disposed along the horizontal axis, and motor numbers are disposed along the vertical axis such that a single cell corresponds to a single pulse motor.

Figure 5:
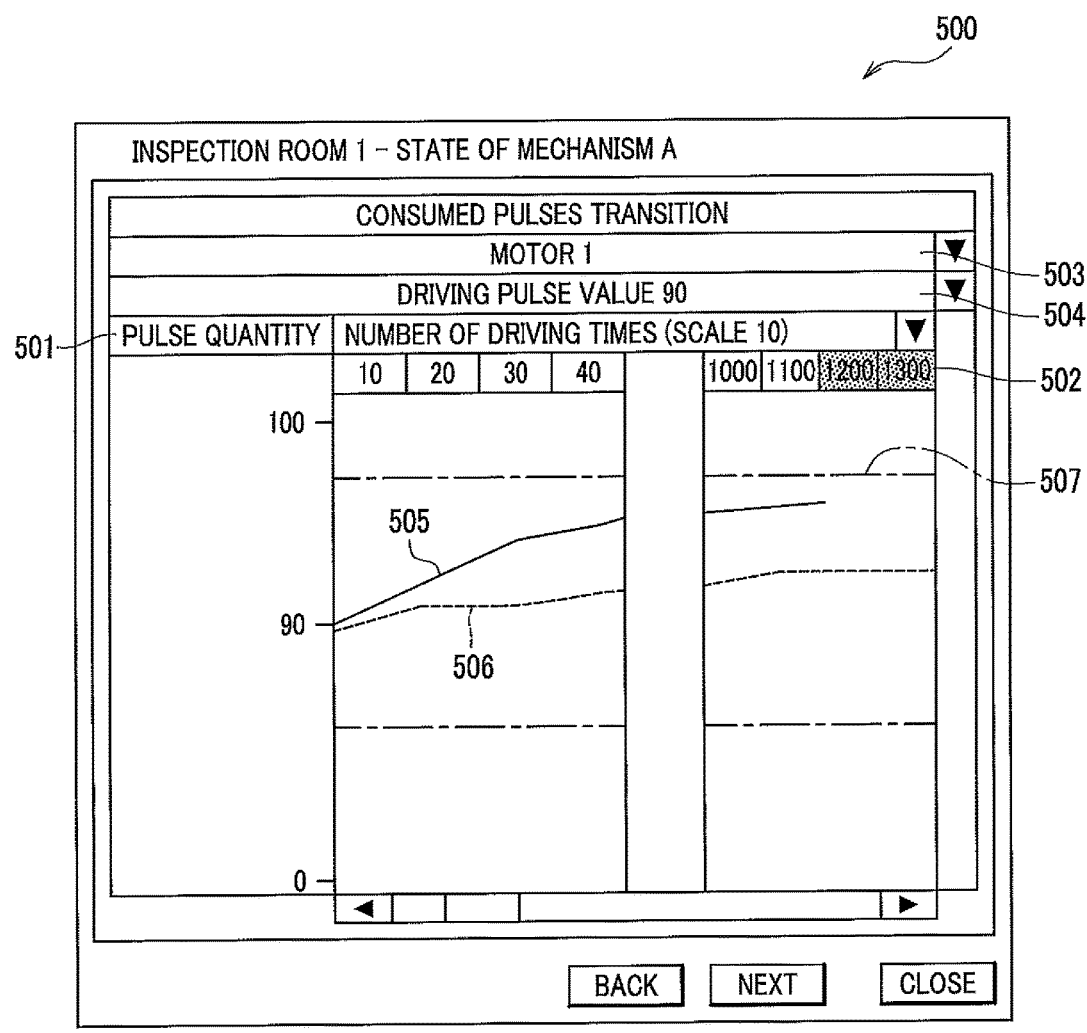
FIG. 5 shows an example of a screen displaying graphs representing variation in a consumed pulse quantity of an individual pulse motor.

A cell of a pulse motor determined, in association with the graphs shown in FIG. 5, to have a possibility of failure occurrence is represented by an indication 603 with a different mark and in a different color. Incidentally, it is also possible to assign different colors or marks depending on whether the determination has been made by deviation from the average consumed pulse quantity or by approximation to the average at-failure pulse quantity.

Incidentally, in the screen 600 in FIG. 6, by selection of the cell corresponding to a pulse motor, a screen 500 (see FIG. 5) displaying variation in the consumed pulse quantity of an individual pulse motor is displayed.

(Screen for Displaying States of Automatic Analysis Devices)

In the following, an example of a screen 700, displayed on the user terminal 204, for displaying the states of automatic analysis devices will be described, referring to FIG. 7.

The screen 700 shown in FIG. 7 is displayed in a matrix structure 701 in which the numbers of inspection rooms are disposed along the vertical axis and the numbers of automatic analysis devices in the respective inspection rooms are disposed along the horizontal axis such that a single cell corresponds to a single automatic analysis device.

A cell of an automatic analysis device having a pulse motor determined, in association with the graphs shown in FIG. 5, to have a possibility of failure occurrence is represented by an indication 702 with a different mark and in a different color. Incidentally, it is also possible to assign different colors or marks depending on whether the determination has been made by deviation from the average consumed pulse quantity or by approximation to the failure average pulse quantity.

Incidentally, in the screen 700 in FIG. 7, by selection of the cell corresponding to an automatic analysis device, a screen 600 (see FIG. 6) displaying the states of pulse motors of the corresponding individual automatic analysis device is displayed.

(Input Screen for Input of Deviation Rate and Approximation Rate)

In the following, an example of an input screen 800, displayed on the user terminal 204, for input of a deviation rate and an approximation rate will be descried, referring to FIG. 8.

The input screen shown in FIG. 8 allows switching between input of a deviation rate and input of an approximation rate by pull-down 801, and allows switching between models of automatic analysis device by pull-down 802.

The screen is displayed in a matrix structure 803, in which the respective mechanisms of an automatic analysis device are disposed along the horizontal axis and the numbers of motors are disposed along the vertical axis, for an individual model of automatic analysis device selected via the pull-down 802 such that a single cell corresponds to a single pulse motor.

Then, by inputting a numeric value into a cell 804 corresponding to the pulse motor, a deviation rate or an approximation rate selected via the pull-down 801 can be input.

Incidentally, a deviation rate or an approximation rate having been input via the input screen 800 is stored via the WEB server 203 and the communication line 206 into the deviation rate 407 or the approximation rate 408 of the pulse motor average value table 400 (see FIG. 4) of the maintenance server 202.

(Process by Maintenance Server 202)

Figure 9:
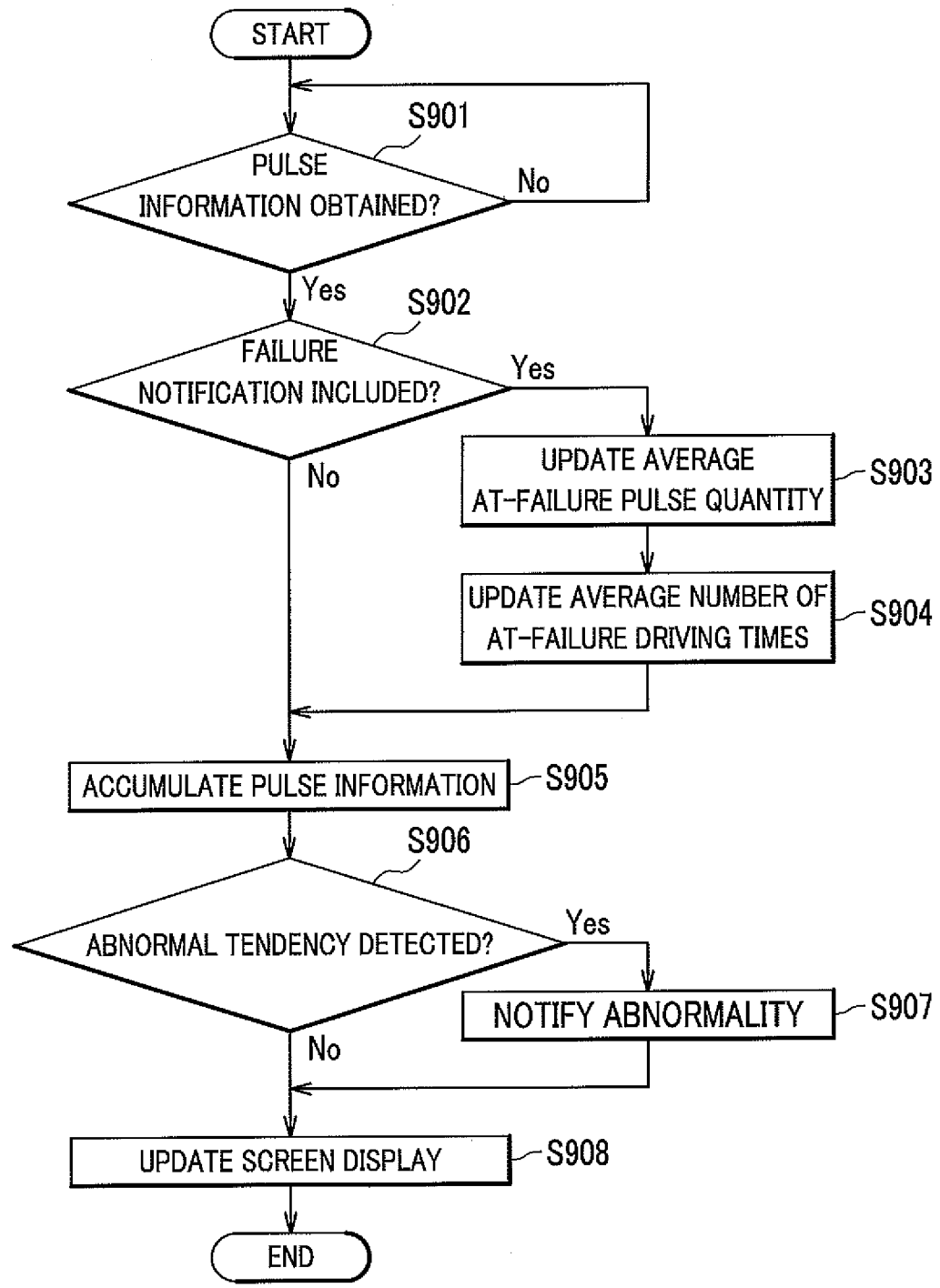
FIG. 9 is a flowchart showing a process by the maintenance server.

In the following, a process by the maintenance server 202 will be described, referring to FIG. 9. FIG. 9 is a flowchart showing the process by the maintenance server 202.

First, an automatic analysis device 100 is configured to be able to transmit a telegram message in which pulse information (driving pulse value, consumed pulse quantity, remaining pulse quantity), the number of driving times, and the failure state of a pulse motor are stored.

In step S901, the maintenance server 202 determines whether or not it has received, from an automatic analysis device 100, a telegram message including pulse information (driving pulse value, consumed pulse quantity, remaining pulse quantity), the number of driving times, and a failure state. If the maintenance server 202 has not yet received a telegram message including pulse information (S901, No), the maintenance server 202 repeats step S901 until it obtains such a telegram message. When the maintenance server 202 has obtained a telegram message including pulse information (S901, Yes), the process by the maintenance server 202 proceeds to step S902.

In step S902, the maintenance server 202 determines whether or not the telegram message, obtained in step S901, including pulse information includes a notification representing that the failure state of the pulse motor is failure. If a notification of the failure of the pulse motor is included (S902, Yes), the process by the maintenance server 202 proceeds to step S903. If a notification of failure of the pulse motor is not included (S902, No), the process by the maintenance server 202 proceeds to step S905.

In step S903, the maintenance server 202 computes an average value, based on the consumed pulse quantity obtained in step S901 and at-failure consumed pulse quantities in the past, and updates the average at-failure pulse quantities 406 of the pulse motor average value table 400 (see FIG. 4).

In step S904, the maintenance server 202 computes an average value, based on the number of driving times in the telegram message obtained in step S901 and the numbers of at-failure driving times in the past, and updates the average number of at-failure driving times 405 in the pulse motor average value table 400 (see FIG. 4). Then, the process by the maintenance server 202 proceeds to step S905.

In step S905, the maintenance server 202 accumulates the pulse information and the number of driving times obtained in step S901 into the pulse information table 300 (see FIG. 3). Herein, if the pulse motor is not in failure, the maintenance server 202 computes the average consumed pulse quantity (see graph 506 in FIG. 5) of the same pulse motors (pulse motors being of the same model and installed at the same position of the same mechanism), as the pulse motor to be the object, in all the facilities as the object of averaging computation.

In step S906, the maintenance server 202 detects the abnormal tendency of a pulse motor. Concretely, if the consumed pulse quantity obtained in step S901 deviates at a larger rate than the deviation rate 407 (see FIG. 4) from the average consumed pulse quantity (see graph 506 in FIG. 5), a possibility of failure occurrence is determined, and an abnormal tendency is thus detected. Further, if the consumed pulse quantity obtained in step S901 approximates to the average at-failure pulse quantity 406 (see FIG. 4) at the approximation rate 408 (see FIG. 4), a possibility of failure occurrence on the pulse motor is determined, and an abnormal tendency is thus detected.

If an abnormal tendency is detected (S906, Yes), the process by the maintenance server 202 proceeds to step S907. If an abnormal tendency is not detected (S906, No), the process by the maintenance server 202 proceeds to step S908.

In step S907, the maintenance server 202 notifies the user terminal 204 of abnormality. Then, the process by the maintenance server 202 proceeds to step S908.

In step S908, the maintenance server 202 updates the screens 500, 600, and 700 (see FIG. 5, FIG. 6, and FIG. 7), and transmits them to the WEB server 203.

In such a manner, the maintenance server 202 is configured to obtain pulse information from an automatic analysis device 100, detect abnormal tendency of a pulse motor (possibility of failure occurrence), and notify the user terminal 204 of it.

Therefore by adding a mechanism of an automatic analysis device 100 on which an abnormal tendency has been detected to check items of periodic inspection, it is possible to prevent failure occurrence on a pulse motor, and reduce the down time of an automatic analysis device 100 occurring during a cycle of periodic inspections.

Further, the average number of at-failure driving times 405 (see FIG. 4) is updated in real time, and it is thereby possible to appropriately predict a time of component replacement and specify a mechanism that needs improvement. Still further, it is possible to detect a mechanism with a high failure frequency in an automatic analysis device 100, and thereby obtain a target of improvement in an automatic analysis device in operation or an automatic analysis device under development.

Modified Examples

Incidentally, an automatic analysis device and a maintenance support system in the present embodiment are not limited to the arrangement in the foregoing embodiment, and various changes and modifications can be made in a range without departing from the purpose of the invention.

It has been described that a driving pulse value, a consumed pulse quantity, and a remaining pulse quantity are transmitted as pulse information from an automatic analysis device 100 to the maintenance support system 200, however, the invention is not limited thereto. When any two out of the driving pulse value, the consumed pulse quantity, and the remaining pulse quantity are known to satisfy the relationship represented by the above-described Expression (1), the remaining one can be computed by Expression (1). Accordingly, arrangement may be made such that any two out of a driving pulse value, a consumed pulse quantity, and a remaining pulse quantity are transmitted as pulse information from an automatic analysis device 100 to the maintenance support system 200, and information of the remaining one is computed by Expression (1) on the maintenance support system 200.

It has been described that the maintenance server 202 detects an abnormal tendency (see S906 in FIG. 9), based on a consumed pulse quantity, however, the invention is not limited thereto.

For example, an abnormal tendency may be detected, based on a remaining pulse quantity. That is, when the remaining pulse quantity of a pulse motor as an object has deviated from the average value of the remaining pulse quantities of pulse motors in all the inspection rooms by a predetermined quantity or more or has approximated to the average value of at-failure-occurrence remaining pulse quantities by a predetermined quantity or more, the maintenance server 202 determines that the pulse motor has a possibility of failure occurrence, and thus detects an abnormal tendency.

DESCRIPTION OF REFERENCE SYMBOLS

100 . . . automatic analysis device (mechanisms driven by pulse motors)
103 . . . rack transportation device (a mechanism driven by a pulse motor)
104 . . . specimen dispensing mechanism (a mechanism driven by a pulse motor)
106 . . . reaction disc (a mechanism driven by a pulse motor)
110 . . . reagent disc (a mechanism driven by a pulse motor)
111 . . . reagent dispensing mechanism (a mechanism driven by a pulse motor)
112 . . . agitation device (a mechanism driven by a pulse motor)
113 . . . cleaning device (a mechanism driven by a pulse motor)
117 . . . computer (transmitting means)
118 . . . interface (transmitting means)
200 . . . maintenance support system
202 . . . maintenance server
203 . . . WEB server
204 . . . user terminal
300 . . . pulse information table 304 . . . number of driving times
305 . . . pulse information
400 . . . pulse motor average value table
405 . . . average number of at-failure driving times
406 . . . average at-failure pulse quantity
407 . . . deviation rate (deviation rate from average pulse quantity)
408 . . . approximation rate (approximation rate to at-failure pulse quantity)
505 . . . consumed pulse quantity
506 . . . average consumed pulse quantity
507 . . . average at-failure pulse quantity
800 . . . input screen (setting means)

The invention claimed is:

1. A maintenance support system comprising:
a maintenance server communicably connected to a plurality of automatic analysis devices, each including a plurality of pulse motors, a plurality of mechanisms each driven by a different one of the pulse motors and a computer connected to each of the pulse motors to control driving of the mechanisms,
wherein the maintenance server is programmed to:
obtain, from each one of the analysis devices, pulse information including a plurality of consumed pulse quantities which are each a quantity of pulses having been consumed during actual driving of a respective one of the pulse motors of the respective one of the analysis devices, and one of a plurality of driving pulse values for driving the respective ones of the pulse motors and a plurality of remaining pulse quantities for the respective ones of the pulse motors, where a relationship is satisfied that a corresponding one of the consumed pulse quantities subtracted from a corresponding one of the driving pulse values is equal to a corresponding one of the remaining pulse quantities for each of the respective pulse motors;
determine whether or not one of the obtained consumed pulse quantities of a first one of the pulse motors deviates, by more than a predetermined deviation rate, from an average consumed pulse quantity that is an average value of the obtained consumed pulse quantities of the pulse motors of a same type in different ones of the analysis devices and which have the driving pulse values which are a same value as the corresponding one of the driving pulse values of the first one of the pulse motors; and
output a notification that the first one of the pulse motors is abnormal when the deviation of the first one of the pulse motors has been determined.

2. The maintenance support system according to claim 1, wherein the maintenance server is further programmed to:
determine whether or not the one of the obtained consumed pulse quantities of the first one of the pulse motors approximates to an average at-failure pulse quantity by more than a predetermined approximation rate, the average at-failure pulse quantity being an average value of the obtained consumed pulse quantities at failure occurrence of the pulse motors of the same type in different ones of the analysis devices, and
output a notification that the first one of the pulse motors is abnormal when the approximation has been determined.

3. The maintenance support system according to claim 2, further comprising:
a web server communicably connected to the maintenance server; and
a user terminal communicably connected to the web server that includes a display,
wherein the maintenance server is further programmed to generate graphical user interface screen information for setting the predetermined approximation rate and send the graphical user interface screen information to the web server,
wherein the web server stores the graphical user interface screen information, and
wherein the graphical user interface screen information is displayed on the display of the user terminal and receives an input for setting the predetermined approximation rate.

4. The maintenance support system according to claim 2, wherein the maintenance server is further programmed to generate a display screen for graphically displaying the consumed pulse quantities of the pulse motors, the average consumed pulse quantities, and the average at-failure pulse quantities.

5. The maintenance support system according to claim 1, further comprising:
a web server communicably connected to the maintenance server; and
a user terminal communicably connected to the web server that includes a display,
wherein the maintenance server is further programmed to generate display screen information for displaying a graphical representation of each of the automatic analysis devices and displaying an indication of which one of the automatic analysis devices includes the first one of the pulse motors determined to be abnormal, and send the display screen information to the web server,
wherein the web server stores the display screen information, and
wherein the display screen information is displayed on the display of the user terminal,
wherein the indication is displayed by one of highlighting of the graphical representation of the one of the automatic analysis devices that includes the first one of the pulse motors determined to be abnormal and displaying the graphical representation of the one of the automatic analysis devices that includes the first one of the pulse motors determined to be abnormal in a different color than other graphical representations of the automatic analysis devices.

6. The maintenance support system according to claim 1, further comprising:
a web server communicably connected to the maintenance server; and
a user terminal communicably connected to the web server that includes a display,
wherein the maintenance server is further programmed to generate graphical user interface screen information for setting the predetermined deviation rate and send the graphical user interface screen information to the web server,
wherein the web server stores the graphical user interface screen information, and
wherein the graphical user interface screen information is displayed on the display of the user terminal and receives an input for setting the predetermined deviation rate.

7. A method of a maintenance support system including a plurality of automatic analysis devices, each including a plurality of pulse motors, a plurality of mechanisms each driven by a different one of the pulse motors, and a computer connected to a storage device and to each of the pulse motors to control driving of the mechanisms; and a maintenance server communicably connected to each of the analysis devices, the method comprising the steps of:

obtaining, by the maintenance server from each one of the analysis devices, pulse information including a plurality of consumed pulse quantities which are each a quantity of pulses having been consumed during actual driving of a respective one of the pulse motors of the respective one of the analysis devices, and one of a plurality of driving pulse values for driving the respective ones of the pulse motors and a plurality of remaining pulse quantities for the respective ones of the pulse motors, where a relationship is satisfied that a corresponding one of the consumed pulse quantities subtracted from a corresponding one of the driving pulse values is equal to a corresponding one of the remaining pulse quantities for each of the respective pulse motors;

determining, by the maintenance server, whether or not one of the obtained consumed pulse quantities of a first one of the pulse motors deviates, by more than a predetermined deviation rate, from an average consumed pulse quantity that is an average value of the obtained consumed pulse quantities of the pulse motors of a same type in different ones of the analysis devices and which have the driving pulse values which are a same value as the corresponding one of the driving pulse values of the first one of the pulse motors; and outputting a notification, by the maintenance server, that the first one of the pulse motors is abnormal when the deviation of the first one of the pulse motors has been determined.

8. The maintenance support system method according to claim 7, further comprising the steps of:

determining, by the maintenance server, whether or not the one of the obtained consumed pulse quantities of the first one of the pulse motors approximates to an average at-failure pulse quantity by more than a predetermined approximation rate, the average at-failure pulse quantity being an average value of the obtained consumed pulse quantities at failure occurrence of the pulse motors of the same type in different ones of the analysis devices, and outputting a notification, by the maintenance server, that the first one of the pulse motors is abnormal when the approximation has been determined.

9. The maintenance support system method according to claim 8, further comprising the steps of:

generating, by the maintenance server, a display screen for displaying the remaining pulse quantities of the pulse motors, the average remaining pulse quantities, and the average at-failure pulse quantities.

10. The maintenance support system method according to claim 8, further comprising the steps of:

generating, by the maintenance server, graphical user interface screen information setting means for setting the predetermined approximation rate, and sending the graphical user interface screen information to a web server, storing, by the web server, the graphical user interface screen information, and displaying on a display, by a user terminal, the graphical user interface screen and receiving an input for setting the predetermined approximation rate.

11. The maintenance support system method according to claim 7, further comprising the steps of:

generating, by the maintenance server, graphical user interface screen information for setting the predetermined deviation rate and sending the graphical user interface screen information to a web server, storing, by the web server, the graphical user interface screen information, and displaying on a display, by a user terminal, the graphical user interface screen and receiving an input for setting the predetermined deviation rate.

12. The maintenance support method according to claim 7, further comprising the steps of:

generating, by the maintenance server, display screen information for displaying a graphical representation of each of the automatic analysis devices and displaying an indication of which one of the automatic analysis devices includes the first one of the pulse motors determined to be abnormal, and sending the display screen information to the web server;

storing, by a web server, the display screen information; and displaying, by a user terminal, the display screen information, and wherein the indication is displayed by one of highlighting of the graphical representation of the one of the automatic analysis devices that includes the first one of the pulse motors determined to be abnormal and displaying the graphical representation of the one of the automatic analysis devices that includes the first one of the pulse motors determined to be abnormal in a different color than other graphical representations of the automatic analysis devices.

* * * * *